(12) United States Patent
Ricci et al.

(10) Patent No.: US 6,224,635 B1
(45) Date of Patent: May 1, 2001

(54) IMPLANTATION OF SURGICAL IMPLANTS WITH CALCIUM SULFATE

(75) Inventors: John Ricci, Middletown; Harold Alexander, Short Hills, both of NJ (US); Charles L. Berman; Sally Frenkel, both of New York, NY (US); Bruce Hollander, Deerfield Beach, FL (US); Gabriele Pecora, Rome (IT)

(73) Assignee: Hospital For Joint Diseases, New York, NY (US)

( * ) Notice: Subject to any disclaimer, the term of this patent is extended or adjusted under 35 U.S.C. 154(b) by 0 days.

(21) Appl. No.: 09/187,584

(22) Filed: Nov. 6, 1998

(51) Int. Cl.[7] .................................. A61K 6/08; A61F 2/28
(52) U.S. Cl. ..................................... 623/23.62; 623/23.51; 424/426; 523/116
(58) Field of Search .............................. 623/23.51, 23.61, 623/23.62, 23.75, 23.76; 424/426; 523/116

(56) References Cited

U.S. PATENT DOCUMENTS

| | | |
|---|---|---|
| 2,247,572 | 7/1941 | Collins . |
| 3,746,680 | 7/1973 | Boricheski . |
| 4,192,021 | 3/1980 | Deibig et al. . |
| 4,356,572 | 11/1982 | Guillemin et al. . |
| 4,381,947 | 5/1983 | Pellico . |
| 4,526,619 | 7/1985 | Ohi et al. . |
| 4,535,485 | 8/1985 | Ashman et al. . |
| 4,969,906 | 11/1990 | Kronman . |
| 5,039,546 | 8/1991 | Chung et al. . |
| 5,478,355 | 12/1995 | Muth et al. . |
| 5,571,188 | 11/1996 | Ellingsen et al. . |
| 5,776,382 | * 7/1998 | Kim et al. ............................... 264/16 |
| 6,030,636 | * 2/2000 | Randolph et al. .................... 424/426 |

* cited by examiner

Primary Examiner—Paul B. Prebilic
(74) Attorney, Agent, or Firm—Stephen E. Feldman; M. K. Silverman

(57) ABSTRACT

The present invention relates to techniques for the preparation and implantation of implants with surgical cements composed primarily of calcium sulfate ("CS"). The first of these novel techniques involves the steps of: (1.) precoating an implant with CS; (2.) permitting the implant to dry, and, (3.) thereafter grouting the implant in place with wet CS. The second embodiment involves: (1.) grouting an uncoated implant in place with wet CS. Finally, the third embodiment involves: (1.) precoating an implant with CS; (2.) permitting it to dry; and, (2.) subsequently press-fitting the implant in place without grouting.

22 Claims, No Drawings

IMPLANTATION OF SURGICAL IMPLANTS WITH CALCIUM SULFATE

FIELD OF THE INVENTION

This invention relates to the implantation of surgical implants by novel techniques that employ a surgical cement primarily composed of calcium forms of sulfate which have a solubility in water (pure water) at 25° C. in the range of about $0.5 \times 10^{-2}$ M to about $20 \times 10^{-2}$ M (hereinafter referred to as "CS"). There are at least three types of CS which are particularly useful in the present invention. These are calcium sulfate dihydrate, calcium sulfate hemihydrate and anhydrous calcium sulfate. Of these, the most preferred species is calcium sulfate hemihydrate. These novel techniques are described in detail below.

BACKGROUND OF THE INVENTION

The present invention is particularly of interest in the treatment of titanium or titanium alloy, such as Ti/Al/V alloy, implants, but may also be employed for the treatment of other metallic implants such as those of zirconium and tantalum, and coated metallic implants such as hydroxyapatite-coated titanium.

Dental Implants

Although the instant invention also contemplates orthopedic bone implants, it is equally applicable to dental bone implants.

There are basically two types of dental implants. Those that sit on top of the jaw bone, but under the gums, and those that fit into the jawbone similar to the root of a natural tooth. Each type offers solid, non-mobile support for replacement teeth which act and feel like natural teeth. Since both types are attached to the patient's jawbone they can provide distinct advantages over traditional methods of replacing missing teeth.

There are generally four types of dental bone grafts used: autograflts are those where the bone to be grafted to the jaw is taken, or harvested, from the patient's own body. The area where the bone is harvested from, known as the donor site, is usually the mouth or the hip. This is the paticnt's own bone and is very compatible with the patient's body. Autografts are generally the best graft technique and usually result in the greatest regeneration of nissing jawbone. Allografts are taken from human donors. Many countries have donor programs where you can specify that in the event of the patient's death, parts may be harvested from the patient's body to save or improve the life of others. Heart transplants are one type of allograft. This can represent one of the greatest "gifts" you can ever give. Bone obtained in this manor undergoes rigorous tests and sterilization. The patient's body "converts" the donor bone into the patient's natural bone, thereby rebuilding the patient's resorbed jawbone.

Xenografts are harvested from animals. The animal bone, most cormnonly bovine (cow), is specially processed to make it biocompatible and sterile. It acts like a "filler" which in time the patient's body will replace with natural bone. After this replacement process is complete dental implants may be placed to support teeth.

Alloplastic grafts are inert, man made synthetic materials. The modern artificial joint replacement procedure uses metal alloplastic grafts. For bone replacement a man made material that mimics natural bone is used. Most often this a form of calcium phosphate. Depending on how it is made, it may be "resorbable" or "non-resorbable". That is, the patient's body may or may not replace the alloplastic graft with the patient's natural bone. In those cases where it is not replaced it acts as a lattice or scaffold upon which natural bone is built. In either case, the end result is to create enough bone for the placement of dental implants.

There are many implants available, each designed for a specific function. Most are made of titanium, an inert metal which has been proven to be effective at fusing with living bone, a process known as "osseointegration". The cylindrical or screw type implant, called "root form", is similar in shape to the root of a tooth with a surface area designed to promote good attachment to the bone. It is the most widely used design and generally placed where there is plentiful width and depth of jawbone. Where the jawbone is too narrow or short for immediate placement of root form implants the area may be enhanced with bone grafting to allow for their placement.

When the jawbone is too narrow and not a good candidate for bone grafting, a special narrow implant, called "plate form", can be placed into the bone. In cases of advanced bone loss, the "subperiosteal" implant, may be prescribed. It rests on top of the bone but under the gums.

The actual implant procedure involves the surgical placement of the implant or implants, a healing period (osseointegration) and implant restoration to replace the missing tooth or teeth.

The treatment may be a cooperative effort between a surgical dentist who actually places the implant and a restorative dentist who designs, prescribes and inserts the final replacement teeth. Some dentists have advanced training and provide both of these services.

Root form implants are the closest is shape and size to the natural tooth root. They are commonly used in wide, deep bone to provide a base for replacement of one, several or a complete arch of teeth. After application of anesthetic, the patient's dentist will expose the area of the jawbone to be implanted and prepare the bone to accept the implant. The number of incisions and bone preparations depends upon the number of implants (and teeth) being placed. The implant is carefully set into place and the gums are closed with several stitches. The healing period usually varies from as few as three months to six or more. During this time osseointegration occurs. The bone grows in and around the implant creating a strong structural support. In fact, this bond can be even stronger than the original tooth's. When healing is complete, the patient's implant is uncovered and an extension or abutment is attached to it. Now the implant and abutment act as a solid unit ready to support the patient's new tooth or teeth.

Plate form implants are usually used when the bone is so narrow it may not be suitable for the root form implant and the area is not suitable for bone grafting. The plate form implant is flat and long so it can fit into the narrow jawbone. After application of anesthetic, the patient's dentist will expose the area of the jawbone to be implanted and prepare the bone to accept the shape of the implant. The number of incisions depends upon the number of implants being placed. The implant is carefully set into place and the gums are closed with several stitches. Like root form implants, there is usually a healing period for osseointegration, although some plate form implants are designed for immediate restoration.

With very advanced jawbone resorption there may not be enough bone width or height for the root form or plate form implant. In these cases the subperiosteal implant may be prescribed. The subperiosteal implant is custom made and designed to sit on top of the bone, but under the gums. There are two methods for its placement. After application of anesthetic, the patient's dentist will expose the jawbone and take an impression or model of the bone using special materials. This model is used by a dental laboratory to carefully create the custom implant to fit the patient's jaw. A second procedure is then carried out where the jawbone is exposed and the implant placed. The gums are closed with several stitches and replacement teeth are put into place.

For the "single surgery" method the patient's dentist will order a special CAT scan of the patient's jawbone Using the CAT scan data and advanced computer modeling techniques, a model of the patient's jawbone is constructed. This model is used by a dental laboratory to fabricate the custom subperiosteal implant to fit the patient's jaw. A surgical procedure is then carried out where the jawbone is exposed and the implant placed. The gums are closed with several stitches and the replacement teeth are put into place.

Bone Implants

Owing to the rapid development of surgery, it is nowadays possible to carry out operations to bones and joints which were still inconceivable a little while ago. For example, it is now possible to carry out surgical removal of cysts, foci of suppuration in bone and malignant tumors from bones. This results in defects in the bone, which need to be filled since normal bone repair processes are no longer able to compensate them. Some defects of this type may have a volume of up to 600 cm$^3$ which has to be filled again.

For filling cavities of this type use is made of bone replacement materials in liquid, pasty or solid form as granules or articles for implantation. If the cavities which are to be filled are not too large then the purpose of the bone replacement materials is to temporarily fill the cavities in the bone and to allow the body itself to compensate, in the course of time, the defect with living bone material.

This may entail there being either growth around the replacement material, which stays in place without irritation, or slow breakdown and replacement thereof by living bone.

It is necessary to use a material which is compatible with bone for filling larger cavities with bone replacement material. The materials of this type which are used are endogenous or exogenous fragments of bone or bydroxyapatite granules. Only very limited amounts of endogenous bone material are available, and additional surgical operations are necessary to obtain it. It is necessary to remove all antigens from exogenous, for example animal, bone materials in order to avoid rejection reactions, but this is only partially successful in practice.

When hydroxyapatite is used there is primarily irritation of the surrounding bone material. When this occurs a material in the form of a liquid, pasty or solid can be used for filling cavities in bones, that is to say for filling bone defects and which does not cause any primary irritations.

Bone implants are frequently used in surgical operations. Bone implants are items which are implanted in the bones of the body of a recipient and permanently replace parts of the skeleton or roots of teeth. The outer layer of the bone implant, which comes into contact with the living substrate bone, is termed the bone-contact layer. At the present time, metals, such as, for example, special steels, noble metals, titanium, ceramic materials, such as, for example, alumina, glass-eramics, hydroxy-apatite ceramics and synthetic materials are used as bone implants and as bone-contact layers.

These substances are classified as biocompatible and bioactive according to the tissue compatibility. Biocompatible substances are tolerated by the body in the long term without rejection. Bioactive substances become rigidly incorporated like endogenous tissue, the tissue compatibility being determined by the chemical composition, the crystalline structure, the surface structure and the mechanical properties.

The metals and some ceramic materials, such as, for example, alumina ceramics, are biocompatible. Ensheathing by connective tissue always takes place in the body. This connective tissue layer allows the implant to be held relatively rigidly, but does not allow frictional connection to the mineral framework of the substrate bone.

Because of the absence of primary integration into the substrate bone, a biocompatible implant of this type can be exposed to only slight mechanical stress since otherwise it is held increasingly poorly, and this is associated with pain and, finally, the loss of the implant. This is found, for example, with hipjoint prostheses, which are always subject to great stress and for which nowadays more than one quarter of the operations are carnied out because of loosening of an implant which had previously been inserted.

Thus, additional undercutting such as, for example, a screw thread is necessary for permanent mechanical anchoring of biocompatible implants in bone. With all metallic implants it is still an unanswered question of whether they release toxic metal ions into the surroundings and thus may have adverse effects in the long term.

Even when bone cement is used, despite the initially better mechanical connection to the substrate bone, a loosening which has been described takes place, with some delay.

In the case of bioactive materials, after some time the bone material grows directly on such materials. Among the known materials, the best properties in this respect are shown by hydroxyapatite which, after a period, which lasts only a few weeks, of mild signs of irritation, which can be detected under the microscope by giant cells around the implant, is integrated into the substrate bone without an interlayer.

As a general rule, bioactive materials are difficult to work and less mechanically stable than the biocompatible metals or ceramics.

Thus, there has been a shift by the medical profession to the use of combined implants comprising biocompatible cores such as, for example, titanium, special steel and alumina, and bioactive surface coatings (compare German Patent Specification No. 2,840,064). A combined implant construction of this type may have considerable advantages since, in this case, high mechanical stability of complex-shaped implants is combined with rapid and rigid connection to the substrate bone. As indicated above, signs of irritation appear after the insertion of implants of this type with the bioactive coatings hitherto known, but these signs subside after some time. Thus, there exists a great need for a treatment which can be used to promote the production of new bone tissue and accelerate the healing process around such implants It is contemplated by the present invention that any or all of the foregoing implants may include areas of microgeometry as disclosed in the copending application Ser. No. 08/996,244, filed Dec. 22, 1997; all valid portions thereof, incorporated herein by reference.

DESCRIPTION OF THE PRIOR ART

In about the last Twenty (20) years, implant techniques that employ many artificial hard tissue materials have been used surgeons. Among these materials, bioglass and bioceramics, such as hydroxyapatite and beta-tricalcium phosphate, have excellent biocompatibility. Most of the bioglass and bioceramics for medical applications are prepared either in granule form or block form. The granule form has mobility problems and relatively poor manipulation characteristics, while the block form is quite brittle and difficult to shape. Many other techniques have been attempted to solve the above-noted problems. Various of these techniques have employed other materials such as. Plaster of Paris, collagen, different types of calcium phosphate grout or cement, polylactates and polyacrylate cement compositions. None of these have been completely acceptable.

The surgeon is most interested in implant techniques that employ materials that can be shaped and hardened in situ. Ideally, an effective implant technique should employ a surgical cement or binder system for hard tissue applications, having the following characteristics: good biocompatibility, a suitable resorption rate, be moldable at the surgical site, and have a controllable setting time with good setting characteristics.

Most currently techniques employing available surgical cements and binder composition systems have disadvantages. For example, collagen-hydroxyapatite and polylactate-hydroxyapatite composites can only be made as premolded shapes and cannot be molded at the surgical site.

Plaster of Paris has reasonable setting characteristics but the resorption rate is too fast. Polyacrylate cement is non-resorbable. Polyacrylic acid-calcium phosphate cement is not resorbable and the setting cement is too acidic. Most of the calcium phosphate grouts or cement compositions are prepared by the reaction of calcium phosphate ceramics with an acidic component. See, for example, Bajpai U.S. Pat. No. 4,668,295. In general, these cement compositions are disadvantageously acidic in nature and take a long time to reach a neutral pH. These calcium phosphate grouts or cement compositions either lack satisfactory mechanical strength or are resorbed too slowly. Moreover, most of the previous calcium phosphate cement compositions developed required the use of hydroxyapatite or tricalcium phosphate as the cementing ceramic and phosphoric acid, bifunctional organic acids or other polyfunctional organic acids as setting reagents. These cement compositions are normally very acidic in nature and take a very long time to reach neutral pH. Also, after implantation, these cement compositions may cause irritation and inflammatory reactions. Thus, the surgical techniques employing these materials have not proven to be totally satisfactory.

Biocompatibility has also been the limiting factor in successful applications of implant cement compositions. The most successful artificial implant materials to achieve the excellent biocompatibility have been hydroxyapatite, bioglass, and other calcium phosphate ceramics. Bioglass is a bioactive glass material whose major components are CaO, $SiO_2$ and $P_2O_3$. Minor components may be $Na_2O$, MgO, $Al_2O_3$, $B_2O_3$ and $CaF_2$. A bioactive glass can form a surface layer of hydroxyapatite when soaked in the aqueous environment. Hydroxyapatite and β-tricalcium phosphate ceramics and calcium phosphate containing glass have been extensively studied. Clinical studies confirmed that most of the calcium phosphate ceramics such as hydroxyapatite, tricalcium phosphate, tetra calcium phosphate and dicalcium phosphate have excellent biocompatibility and are well accepted by both hard tissue and soft tissue. The experimental results also indicated that dense hydroxyapatite is non-biorcsorbable while other porous calcium phosphate ceramics are bioresorbable. Surgical techniques employing these materials have not proven all together to be satisfactory.

A survey of the prior art renders the following U.S. patents which are relevant to the present invention:

U.S. Pat. No. 2,247,572 to Collins discloses a dental compost that includes a calcium sulfate binder.

U.S. Pat. No. 3,746,680 to Boricheski teaches Plaster of Paris compositions for making orthopedic casts.

U.S. Pat. No. 4,192,021 to Deibig, et al, relates to a composition for bone replacement or prosthesis comprising a mixture of calcium phosphate and a biogradable polymer.

U.S. Pat. No. 4,356,572 to Guillemin, et al relates to an implant made of coherent material comprising calcium carbonate in crystalline form.

U.S. Pat. No. 4,381,947 to Pellico relates to settable dental alginate compositions comprising calcium sulfate.

U.S. Pat. No. 4,526,619 to Ohi, et al, relates to a gypsum dental composition comprising calcium sulfate and potassium sulfate.

U.S. Pat. No. 4,535.485 to Ashman, et al, teaches a implant for replacement of bone or bony tissue formed by dispersing a crystalline salt such as calcium chloride in a hydrophilic polymeric material.

U.S. Pat. No. 5,039,546 to Chung, discloses a fluoride treatment of hydoxyapatite coated metal implants.

U.S. Pat. No. 5,478,355 to Muth, et al, describes a method for improving in vivo strength retention of a bioabsorbable implantable medical device that includes the use of calcium fluoride.

U.S. Pat. No. 5,571,188 to Ellingsen, et al, relates to a process for treating implants with an aqueous solution sodium fluoride.

U.S. Pat. No. 5,281,265 to Liu, teaches surgical cements that include calcium compounds.

The inventors have found that the techniques disclosed in these U.S. Patents are not totally satisfactory.

In consideration of the foregoing, it would be of clear advantage to provide new surgical techniques which do not embody these prior art disadvantages.

SUMMARY OF THE INVENTION

Various forms of CS as exemplified by the dense β-form of calcium sulfate hemihydrate have known utility as a resorbable implant material for filling bone defects. It is also known that CS is a benign resorbable space-filler that prevents soft tissue from invading a bone defect until bone cells can fill in the defect. Although the dense α and β-forms of calcium sulfate hemihydrate are the most preferred CS of the techniques of the present invention, any CS which have a solubility in water (pure water) at 25° C. in the range of about $0.5\times10^{-2}$ M to about $20\times10^{-2}$ M, preferably about $0.8\times10^{-2}$ M to about $5\times10^{-2}$ M, is suitable.

The inventors have observed that as CS dissolves in vivo it elevates the local calcium ion concentration in the surrounding tissue. The calcium ions thus formed, reacts with body fluids to cause local precipitation of calcium phosphate bone tineral (hereinafter referred to as "CP") Through this mechanism, CP forms in the new soft granulation tissue that forms around the CS as it dissolves and recedes. Since CP is stable in an in vivo environment, these CP deposits provide a matrix for the formation of new ingrowing bone tissue. This CP matrix promotes the growth of bone tissue within the defect. The more soluble CS salt dissolves, thus driving the solution equilibrium in the direction of precipitation of the much less soluble CP salts within a matrix or any other sites provided for CP deposition.

However, the inventors has discovered that this precipitation process is not always consistent. It is thought that since granulation tissue (the weak red tissue that forms under a scab) is immature in nature, calcium diffusion and CP precipitation in the area of granulation tissue is at best, unpredictable.

The inventors have discovered new techniques that employ CS to stimulate bone ingrowth through a bone attachment mechanism similar to those characteristic of hydroxyapatite and bioglasses. These techniques have equal applicability to conventional othopedic or dental implants as well as any other implant that includes the micro-geometry disclosed in implants may include areas of micro-geometry as disclosed in the copending application, Ser. No. 08/996,244, filed Dec. 22, 1997, all valid portions thereof, incorporated herein by reference.

The first technique involves the steps of (1.) precoating an implant with CS; (2.) permitting the implant to dry, and, (3.) thereafter grouting the implant in place with wet CS. The second embodiment involves: (1.) grouting an uncoated implant in place with wet CS. Finally, the third embodiment involves: (1.) precoating an implant with CS; (2.) permitting it to dry; and, (2.) subsequently press-fitting the implant in place without grouting.

DETAILED DESCRIPTION OF THE INVENTION

THE PREFERRED CALCIUM SULFATE SPECIES

The presently useful CS species applicable to the present invention are selected from, for example, calcium salts, which have a solubility in water (pure water) at 25° C. in the range of about $0.5 \times 10^{-2}$ M to about $20 \times 10^{-2}$ M, preferably about $0.8 \times 10^{-2}$ M to about $5 \times 10^{-2}$ M. There are at least three preferred species of calcium sulfate salts which can be used in the present invention. These are calcium sulfate dihydrate, calcium sulfate hemihydrate and anhydrous calcium sulfate Of these, the most preferred species is calcium sulfate hemihydrate. Among these calcium sulfate salts, calcium sulfate hemihydrate has a solubility which is much higher than that of calcium sulfate dihydrate. Plaster of Paris is calcium sulfate hemihydrate. When Plaster of Paris is mixed with water, it will dissolve and recrystallize to form gypsum cement which is mainly calcium sulfate dihydrate. Because of its relatively high solubility, gypsum cement resorbs quickly. In addition, gypsum cement does not by itself form sufficiently cohesive or adhesive pastes.

Optionally, the CS may further be selected from calcium sulfate-containing ceramics. Such ceramics should be such as to permit the desired interaction between the preferred calcium sulfate specie and a accelerator/stabilizer component during paste hardening. In fact, any calcium sulfate-containing component which permits this desired interaction is acceptable for use in the present invention. Among the useful calcium sulfate containing ceramics are calcium sulfate-calcium alkali (such as sodium potassium and the like) phosphate mixed ceramics, and the like and mixtures thereof The precursor mixtures of the present invention preferably may contain about 100 weight parts to about 500 weight parts of calcium sulfate species per 100 weight parts of an optional accelerator/stabilizer component.

The CS used in the present invention can be in the form of particles, such as in the granule form or the powder form. Particle sizes preferably are within the range of about 3 microns to about 200 microns or about 400 microns. For the granule form, particle size is more preferably between about 40 mesh to about 80 mesh. Since the cement formation is believed to involve the dissolution of calcium sulfate and the recrystallization of a less soluble salt, the setting time is a function of the dissolution rate of calcium sulfate. This, in turn, depends on the type and particle size of the calcium sulfate-containing component used. Other factors affecting the setting rate are the amount of water used, and the type of the accelerator/stabilizer component used.

THE OPTIONAL ACCELERATOR/STABILIZER COMPONENT

The optional accelerator/stabilizer component contemplated by the instant invention is a fluoride component is preferably selected from at least one of alkali metal fluorides and alkaline earth fluorides. More preferably the accelerator/stabilizer component is $CaF_2$, KF, NaF, $MF_2$, or mixtures thereof, or any of the foregoing in combination with NaCl and $K_2SO_4$. Of these, $CaF_2$ is most preferred. Fluoride compounds with elements naturally occurring in bone tissue may also be used. The accelerator/stabilizer component may be in the form of fine powder or granule, having a particle size ranging from a few microns to 20 mesh.

OPTIONAL VISCOSITY MODIFIERS

Optionally, the CS of the present invention may further include biocompatible fluid lubricants and/or viscosity modifiers, generally as described in U.S. Pat. No. 4,803,075, the disclosure of which is incorporated herein by reference. Exemplary lubricant components include glycerol glycogen, maltose, and the like. Organic polymer base materials, such as polyethylene glycol and hyaluronic acid as well as nonfibrillar collagen, preferably succinylated collagen, may also act as lubricants. Such lubricants act to modify the viscosity of the compositions, where grouting of the CS is contemplated.

OPTIONAL pH MODIFIERS

Optionally, the surface pH of the setting CS may be decreased by using hydrogen citrate salts or citric acid with alkaline reagents instead of using pure citric acid as the setting reagent. Among the suitable hydrogen citrate salts are: sodium dihydrogen citrate, disodium hydrogen citrate, ammonium dihydrogen citrate, diammonium hydrogen citrate, potassium dihydrogen citrate and dipotassium hydrogen citrate. Alternatively, the pH may also be raised by using citric acid with potassium citrate, ammonium citrate, sodium phosphate, disodium hydrogen phosphate, potassium phosphate, and dipotassium hydrogen phosphate. While the pH of concentrated pure citric acid is normally at 2, the pH modified setting reagent should provide an initial solution pH which is much higher than the pure citric acid, reaching a pH of 3 to 5. Therefore, after setting, the surface pH of the setting cement will initially be near 5 and quickly reach 7 or higher upon hardening.

OPTIONAL FILLERS

Optionally, the CS of the present invention can incorporate biocompatible fillers. Such fillers can be bioresorbable or non-resorbable. The fillers included are preferably substantially inert with respect to the interaction between the preferred calcium sulfate specie and an accelerator/stabilizer component during hardening. Such fillers include, for example, magnesium oxide, calcium carbonate, α-tricalcium phosphate, β-tricalcium phosphate, hydroxyapatite, calcium phosphate apatite, bioglass and other calcium phosphate-containing ceramics, tetra calcium phosphate, tricalcium phosphate, calcium phosphate apatite, dicalcium phosphate, magnesium hydroxide, magnesium oxide, other sparingly calcium organic salts and the like and mixtures thereof. The weight ratio of the fillers to the preferred calcium sulfate species can be up to about 4 to 1. These fillers can be in the form of particles, such as either granules or powder, which preferably have particle sizes in the range of about 3 microns to about 200 microns or about 400 microns.

PREPARATION OF THE COMPOSITION

In the present invention, any two or all of the CS, accelerator/stabilizer and optional components can be premixed. To form cement, the premixed CS, e.g., powder is added to the desired amount of water, for example, in the form of a saline solution, to form a paste. This paste becomes viscous and adhesive or cohesive. After a certain time, the paste sets and hardens. Alternatively, the accelerator/ stabilizer components are mixed with water first. The CS and other components are then mixed with this aqueous mixture to form a paste. In such case, if the accelerator/ stabilizer component is able to dissolve completely in water, a setting solution can be prepared by dissolving the accelerator/stabilizer component first. The premixed CS and other components are then pasted with the setting solution.

In general, the setting time of the present cements can be easily controlled, for example, so that the paste hardens or sets in about 20 minutes or less after the paste, for example, the viscous and cohesive paste, is formed. Beside controllable setting times, the present cements have near neutral or slightly alkaline (pH) surface characteristics. In addition, the composition of the invention can be changed over a relatively wide range so as to provide the flexibility and advantages of controlling the resorption rate.

The techniques of the present invention can be used in orthopedic, maxillofacial and cranial facial surgical applications and in dental applications. These include 1) a hard tissue replacement material such as bone graft, bone defect filler or bone replacement, 2) ridge augmentation, 3) bone fracture fixation, 4) gluing cement for dentistry and orthopedic surgery, 5) root cement, 6) jaw repair, 7) and bone wax substitute.

In general, the setting rate depends on the type, crystal morphology and particle size of the calcium-containing component used as the preferred calcium sulfate specie. In addition, the amount of water, the type and concentration of the accelerator/stabilizer component, and the type and concentration of the strength enhancing component, if any, can also show significant effects on the setting rate. The present surgical cements compositions have workable (reasonable) and controllable setting times, are biocompatible, are easily manipulated, may be formed in situ or in premolded shapes, and have a wide variety of applications.

The strength as well as the setting time of the present CS are directly dependent on the nature and particle size of the optional particulate components, the type and amount of the optional setting reagent, and the solid powder to liquid ratio. In general, with other factors constant, the strength increases as the particle size of the particulate components decreases. The setting time increases as the cementing powder to setting reagent weight ratio decreases.

As earlier described, the first technique involves the steps of (1.) precoating an implant with a wet CS prepared in the manner described above, (2.) permitting the precoated implant to dry; and, (3.) thereafter grouting the implant in place with wet CS also prepared in the manner described above. The second embodiment involves (1.) grouting an uncoated implant in place with wet CS prepared in the manner described above. Lastly, the third embodiment involves: (1.) precoating an implant with CS prepared in the manner described above, (2.) permitting it to dry; and, (2.) subsequently press-fitting the implant in place without grouting.

This invention may be prepared as a kit, comprising a selected cementing powder and setting reagent which when admixed with aqueous solution will form a paste. This paste will harden in a short time and will reach a pH near 7 or higher.

All valid portions of all U.S. Patents cited herein are incorporated herein for the express purpose of enabling the person of ordinary skill in the art to practice the instant invention.

Although the invention has been described with reference to certain preferred embodiments, it will be appreciated that many variations and modifications may be made within the scope of the broad principles of the invention. Hence, it is intended that the preferred embodiments and all of such variations and modifications be included within the scope and spirit of the invention, as defined by the following claims.

Having described a preferred embodiment of the invention, what we claim and desire to secure by U. S. Letters Patent is:

1. A method of implanting a surgical implant within the body of a patient, the method comprising the steps of:
    (a) at a pre-operative site, preparing a wet surgical cement comprised primarily of a calcium sulfate having a solubility in pure water at 25 degrees C. in a range of about $0.5 \times 10^{-2}$ M to about $20 \times 10^{-2}$ M in which said wet surgical cement further comprises an accelerator/ stabilizer component selected from the group consisting of alkali metal fluorides, alkaline earth fluorides, and combinations thereof;
    (b) at a pre-operative site, coating said surgical implant with said wet surgical cement;
    (c) at a pre-operative site, causing said surgical cement to dry upon said implant; and
    (d) at an operative site, grouting said implant and placing said implant into place within the body of said patient using a grouting material composed primarily of said wet surgical cement.

2. A method of implanting a surgical implant within the body of a patient, the method comprising the steps of:
    (a) at a pre-operative site, preparing a wet surgical cement composed primarily of a calcium sulfate having a solubility in pure water at 25 degrees C in a range of about $0.5 \times 10^{-2}$ to about $20 \times 10^{-2}$ M, said surgical cement comprising an accelerator/stabilizer component is a member selected from the group consisting of alkali metal fluorides alkaline earth fluorides, and combinations thereof;
    (b) at a pre-operative site, coating said surgical implant with said wet surgical cement;
    (c) at a pre-operative site, causing said coating of said implant to dry; and
    (d) at an operative site, press fitting said implant in place within the body of said patient.

3. The method of claim 1 wherein said calcium sulfate is a member selected from the group consisting of calcium sulfate dihydrate, calcium sulfate hemihydrate, anhydrous calcium sulfate and mixtures thereof.

4. The method of claim 3, wherein said calcium sulfate is calcium sulfate hemihydrate.

5. The method of claim 1, wherein said accelerator/ stabilizer component is a member selected from the group consisting of $CaF_2$, $NaF$, $MsF_2$, and mixtures thereof.

6. The method of claim 5, wherein said accelerator/ stabilizer component is $CaF_2$.

7. The method of claim 1, wherein said wet cement further comprising a viscosity modifier.

8. The method of claim 7, wherein said viscosity modifier is a member selected from the group consisting of glycerol, glycogen, maltose, polyethylene glycol, hyaluronic acid, nonfibrillar collagen, succinylated collagen, and mixtures thereof.

9. The method of claim 1, further comprising a pH modifier.

10. The method of claim 9, wherein said pH modifier is selected for decreasing pH.

11. The method of claim 10, wherein said pH modifier is a member selected from the group consisting of sodium dihydrogen citrate, disodium hydrogen citrate, ammonium dihydrogen citrate, diammonium hydrogen citrate, potassium dihydrogen citrate, dipotassium hydrogen citrate, and mixtures thereof.

12. The method of claim 9, wherein said pH modifier is selected for increasing pH.

13. The method of claim 12, wherein said pH modifier is a member selected from the group consisting of NaOH, KOH, $NH_4OH$, ammonium citrate, sodium phosphate, disodium hydrogen phosphate, potassium phosphate, dipotassium hydrogen phosphate, and mixtures thereof.

14. The method of claim 2, wherein the accelerator/stabilizer component is a member selected from the group consisting of $CaF_2$, NaF, $MgF_2$, and mixtures thereof.

15. The method of claim 14, wherein the accelerator/stabilizer component is $CaF_2$.

16. The method of claim 2, further comprising a viscosity modifier.

17. The method of claim 16, wherein said viscosity modifier is a member selected from the group consisting of glycerol, glycogen, maltose, polyethylene glycol, hyaluronic acid, nonfibrillar collagen, succinylated collagen, and mixtures thereof.

18. The method of claim 2, further comprising a pH modifier.

19. The method of claim 18, wherein said pH modifier is selected for decreasing pH.

20. The method of claim 19, wherein said pH modifier is a member selected from the group consisting of sodium dihydrogen citrate, disodium hydrogen citrate, ammonium dihydrogen citrate, diammonium hydrogen citrate, potassium dihydrogen citrate, dipotassium hydrogen citrate, and mixtures thereof.

21. The method of claim 18, wherein said pH modifier is selected for increasing pH.

22. The method of claim 21, wherein said pH modifier is a member selected from the group consisting of NaOH, KOH, $NH_4OH$, sodium citrate, potassium citrate, ammonium citrate, sodium phosphate, disodium hydrogen phosphate, potassium phosphate, dipotassium hydrogen phosphate, and mixtures thereof.

\* \* \* \* \*